US00PP27400P3

(12) United States Plant Patent
Meilland

(10) Patent No.: US PP27,400 P3
(45) Date of Patent: Nov. 22, 2016

(54) HYBRID TEA ROSE PLANT NAMED 'MEIHYALFEU'

(50) Latin Name: *Rosa hybrida*
Varietal Denomination: Meihyalfeu

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 28 days.

(21) Appl. No.: 14/121,689

(22) Filed: Oct. 8, 2014

(65) Prior Publication Data

US 2016/0106013 P1 Apr. 14, 2016

(51) Int. Cl.
*A01H 5/02* (2006.01)

(52) U.S. Cl.
USPC ..... Plt./135

(58) Field of Classification Search
USPC ..... Plt./134, 135
See application file for complete search history.

(56) References Cited

PUBLICATIONS

Rose Trials, www.worldrose.org/trials/2012/hague/hague9.asp, last modified Jul. 17, 2012.*

* cited by examiner

*Primary Examiner* — Anne Grunberg
(74) *Attorney, Agent, or Firm* — Buchanan Ingersoll & Rooney PC

(57) ABSTRACT

A new and distinct Hybrid Tea rose plant is provided that commonly commences blooming early in the season and forms abundantly and substantially continuously attractive ocher double blossoms which display a slight fragrance. The growth habit is semi-erect, and strong vegetation is formed. The vegetation is very dense and bears a glossy aspect on the upper surface that contrasts nicely with the blossom coloration. The disease tolerance is very good particularly with respect to black spot. The plant is well suited for providing attractive ornamentation in parks and gardens.

1 Drawing Sheet

Figures 1, 2, 3, 4, 5, 6, 7, 8, 9, 10, 11, 12, 13, 14:
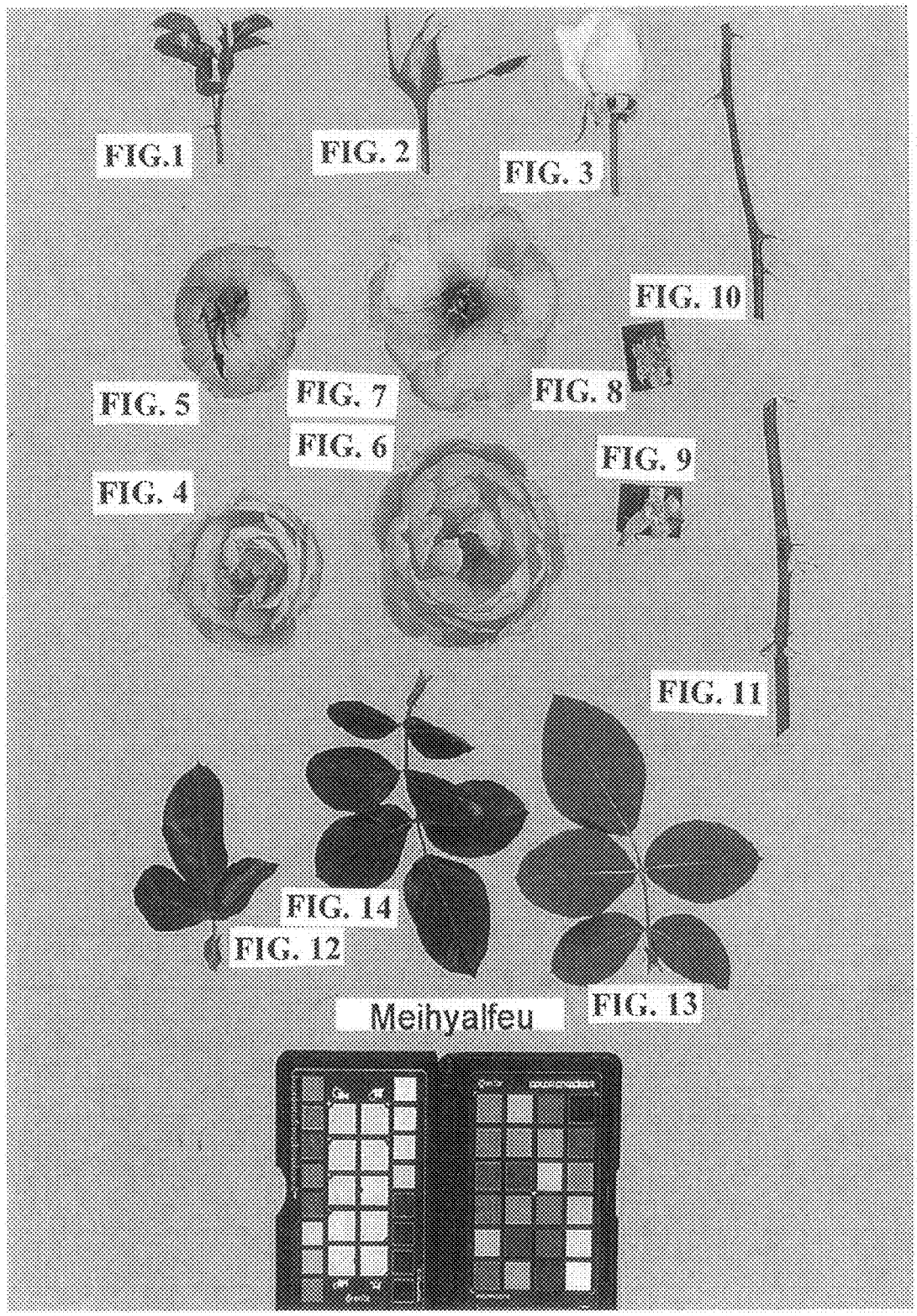

Botanical/commercial classification: *Rosa hybrida*/Hybrid Tea Rose Plant.

Varietal denomination: cv. Meihyalfeu.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meipsilon' variety (non-patented in the United States) and 'Golden Unicorn' variety (non-patented in the United States). The male parent (i.e., the pollen parent) was the 'Meironsse' variety (U.S. Plant Pat. No. 8,496).

The parentage of the new variety can be summarized as follows:

('Meipsilon'×'Golden Unicorn')×'Meironsse'.

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays a semi-erect growth habit with very strong vegetation, (b) forms in abundance on a substantially continuous basis attractive ocher double blossoms which display a slight fragrance, (c) exhibits very dense glossy dark green foliage that contrasts nicely with the blossom coloration, (d) displays very good disease tolerance particularly with respect to black spot, and (e) is well suited for providing attractive ornamentation in parks and gardens.

The blooming tends to commence early in the season, during observations to date.

The new variety well meets the needs of the horticultural industry and can be grown to advantage where attractive ornamentation is to be provided.

The new variety can be readily distinguished from its ancestors. More specifically, the 'Meipsilon' variety forms bicolored red-yellow blossoms, the 'Golden Unicorn' variety forms yellow edged with orange-red blossoms, and the 'Meironsse' variety forms darker Indian Orange edges with Capsicum Red blossoms.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meihyalfeu'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during September while growing outdoors on their own roots at Le Cannet des Maures, Var, France. Standard color information is provided at the bottom of the photograph.

FIG. 1—illustrates a specimen of a young shoot;

FIG. 2—illustrates a specimen of a floral bud at the opening of the sepals;

FIG. 3—illustrates a specimen of a floral bud at the opening of the petals;

FIG. 4—illustrates a specimen of an open flower—plan view—obverse;

FIG. 5—illustrates a specimen of an open flower—plan view—reverse;

FIG. 6—illustrates a specimen of a fully open flower—plan view—obverse;

FIG. 7—illustrates a specimen of a fully open flower—plan view—reverse;

FIG. 8—illustrates a specimen of a floral receptacle showing the arrangement of the stamens and pistils;

FIG. 9—illustrates a specimen of a floral receptacle showing the arrangement of the pistils (stamens removed);

FIG. 10—illustrates a specimen of a flowering stem;

FIG. 11—illustrates a specimen of a main branch;

FIG. 12—illustrates a specimen of a leaf with three leaflets—plan view—upper surface;

FIG. 13—illustrates a specimen of a leaf with five leaflets—plan view—under surface; and FIG. 14—illustrates a specimen of a leaf with five leaflets—plan view—upper surface.

DETAILED BOTANICAL DESCRIPTION

The chart used in the identification of the colors is that of The Royal Horticultural Society (R.H.S. Colour Chart). The description is based on the observation of two-year-old plants during September while growing outdoors on their own roots at Le Cannet des Maures, Var, France.

Class: Hybrid Tea.

Plant:

*Growth habit.*—Semi-erect.

Branches:

*Color.*—Young stems: near Yellow-Green Group 146B. Adult wood: near Yellow-Green Group 146B.

*Thorns.*—On young stems: Small prickles: Quantity: commonly none present. Long prickles: Configuration: with an oval base. Quantity: approximately 6 on average on a stem length of 10 cm. Length: approximately 1.3 cm on average. Color: near Yellow-Green Group 146C. On adult stems: Small prickles: Quantity: commonly none present. Long prickles: Configuration: with an oval base, upright on upper surface and concave on the under surface. Quantity: approximately 8 on average on a stem length of 10 cm. Length: approximately 1.2 cm on average. Color: near Greyed-Orange Group 164B.

Leaves:

*Stipules.*—Adnate, pectinate, rather broad, approximately 1.9 cm in length on average, approximately 0.7 cm in width on average, near Yellow-Green Group 146D on the upper surface, and near Yellow-Green Group 146D on the under surface.

*Petioles.*—Upper surface: near Yellow-Green Group 147A in coloration. Under surface: near Yellow-Green Group 147B in coloration. Length: approximately 3.1 cm on average for the terminal leaflet. Texture: non-glandular on the upper surface, and commonly without prickles on the under surface.

*Rachis.*—Upper surface: near Yellow-Green Group 146C in coloration. Under surface: near Yellow-Green Group 146D in coloration.

*Leaflets.*—Number: 3, 5, 7 (most often), and 9. Shape: generally oval with an cuspidate tip and an obuse base. Size: the terminal leaflets commonly are approximately 7 cm in length on average and approximately 5.5 to 6 cm in width on average. Edges: slightly denticulate. Serration: small and single (as illustrated). Texture: physically firm and leathery. Color (young foliage): Upper surface: near Yellow-Green Group 147A. Under surface: near Yellow-Green Group 147B. Color (adult foliage): Upper surface: near Yellow-Green Group 147A. Under surface: near Yellow-Green Group 147B.

Inflorescence:

*Number of flowers.*—Commonly approximately 1 to 3 blossoms per stem.

*Peduncle.*—Smooth, approximately 7 cm in length on average, approximately 0.5 cm in diameter on average, and near Yellow-Green Group 146C in coloration.

*Sepals.*—Upper surface: tomentose and near Yellow-Green Group 148C in coloration. Under surface: smooth and near Yellow-Green Group 146C to Yellow-Green Group 147D in coloration. Shape: longish and narrow, and rounded at the base. Size: approximately 1.7 to 2 cm in length on average, and approximately 1 cm in width at the widest point on average.

*Buds.*—Shape: substantially conical. Size: large. Length: approximately 2.5 cm on average. Width: approximately 2.5 cm at the widest point on average. Color as calyx breaks: internal petals are near Yellow Group 17C on the upper surface and near Yellow Group 13B suffused with near Orange-Red Group 33C and 33D on the under surface, external petals are near Yellow-Orange Group 15B suffused and margined with near Yellow-Orange Group 19B on the upper surface and near Yellow-Orange Group 15B and 15C suffused with near Orange-Red Group 33D and margined with near Yellow-Orange Group 19B on the under surface, and with a spot at the base of near Yellow-Orange Group 15B on the upper surface.

*Flower.*—Shape: cup-shaped. Diameter: approximately 11 to 12 cm on average. Color (in the course of opening): Upper surface: internal petals are near Yellow-Orange Group 17C, and external petals are near Yellow-Orange Group 15B suffused and margined with near Yellow-Orange Group 19B. Under surface: internal petals are near Yellow Group 13B suffused with near Orange-Red Group 33C and 33D, and external petals are near Yellow-Orange Group 15B and 15C suffused with near Orange-Red Group 33D and margined with Yellow-Orange Group 19B. Color (open flower): Upper side: internal petals are near Yellow-Orange Group 17C and external petals are near Yellow-Orange Group 15B suffused and margined with Yellow-Orange Group 19B. Under side: internal petals are near Yellow Group 13B suffused with near Orange-Red Group 33C and 33D and external petals are near Yellow-Orange Group 15B and 15C suffused with near Orange-Red Group 33D and margined with near Yellow-Orange Group 19B. Fragrance: slight. Spot at base: near Yellow-Orange Group 15B. Petal number: approximately 46 on average under normal growing conditions. Petal shape: with a substantially rounded tip and an obtuse base. Petal texture: leathery and somewhat firm. Petal length: approximately 4.5 cm on average. Petal width: approximately 4.5 cm on average. Petal arrangement: imbricated, and without petaloids. Petal drop: good with the petals commonly detaching cleanly before drying. Stamen number: approximately 94 on average. Anthers: regularly arranged around the styles, approximately 1 mm in size on average, and near Yellow-Orange Group 23B in coloration. Filaments: approximately 6 mm in length on average, and near Yellow-Orange Group 23B in coloration. Pollen: none available for observation. Pistils: approximately 68 on average. Stigmas: approximately 1 mm in size on average, and near Red Group 45B in coloration. Styles: approximately 4 mm in length on average, and near Yellow Group 2D in coloration. Receptacle: smooth, funnel-shaped in longitudinal section, approximately 1.2 cm in length on average, approximately 1 cm in width on average at the widest point, and near Yellow-Green Group 146C in coloration.

Development:

*Vegetation.*—Very strong.

*Blooming.*—Early season, very abundant and substantially continuous.

*Tolerance to diseases.*—Very good particularly with respect to black spot.

The new 'Meihyalfeu' variety has not been observed under all possible environmental conditions to date. Accordingly, it is possible that the phenotypic expression may vary somewhat with changes in light intensity and duration, cultural practices, and other environmental conditions.

I claim:

1. A new and distinct Hybrid Tea rose plant characterized by the following characteristics:

(a) displays a semi-erect growth habit with very strong vegetation, (b) forms in abundance on a substantially continuous basis attractive ocher double blossoms which display a slight fragrance, (c) exhibits very dense glossy dark green foliage that contrasts nicely with the blossom coloration, (d) displays very good tolerance to disease particularly with respect to black spot, and (e) is well suited for providing attractive ornamentation in parks and gardens;

substantially as illustrated and described.

* * * * *

Meihyalfeu